United States Patent
Mon

(10) Patent No.: US 8,765,116 B2
(45) Date of Patent: Jul. 1, 2014

(54) APPARATUS AND METHOD FOR PRE-CONDITIONING/FIXATION AND TREATMENT OF DISEASE WITH HEAT ACTIVATION/RELEASE WITH THERMOACTIVATED DRUGS AND GENE PRODUCTS

(75) Inventor: John Mon, Silver Spring, MD (US)

(73) Assignee: Medifocus, Inc., Columbia, MD (US)

( * ) Notice: Subject to any disclaimer, the term of this patent is extended or adjusted under 35 U.S.C. 154(b) by 1160 days.

(21) Appl. No.: 11/280,199

(22) Filed: Nov. 17, 2005

(65) Prior Publication Data

US 2006/0216275 A1 Sep. 28, 2006

Related U.S. Application Data

(60) Provisional application No. 60/664,699, filed on Mar. 24, 2005.

(51) Int. Cl.
*A61N 1/39* (2006.01)
*A61K 48/00* (2006.01)
*A61K 41/00* (2006.01)
*A61B 18/14* (2006.01)
*A61N 7/02* (2006.01)
*A61B 18/18* (2006.01)

(52) U.S. Cl.
CPC ....... *A61B 18/1477* (2013.01); *A61B 2218/002* (2013.01); *A61B 2018/143* (2013.01); *A61N 7/02* (2013.01); *A61K 41/0052* (2013.01); *A61B 18/18* (2013.01)
USPC .............................. 424/93.2; 514/44 R; 607/1

(58) Field of Classification Search
CPC .............. A61B 18/1477; A61B 18/18; A61B 2018/143; A61B 2218/002; A61K 41/0052; A61N 7/02; B32B 37/146; B32B 3/12; F16L 59/065
USPC ................ 514/34, 44 R; 424/93.1, 93.2, 450; 435/320.1; 607/1
See application file for complete search history.

(56) References Cited

U.S. PATENT DOCUMENTS

| 4,565,200 | A | | 1/1986 | Cosman |
| 4,753,223 | A | * | 6/1988 | Bremer .......................... 600/140 |
| 5,496,271 | A | * | 3/1996 | Burton et al. .................... 607/27 |
| 5,868,740 | A | | 2/1999 | LeVeen et al. |
| 5,928,229 | A | | 7/1999 | Gough et al. |
| 5,954,717 | A | | 9/1999 | Behl et al. |
| 6,050,992 | A | | 4/2000 | Nichols |
| 6,059,780 | A | | 5/2000 | Gough et al. |
| 6,212,433 | B1 | | 4/2001 | Behl |
| 6,235,023 | B1 | | 5/2001 | Lee et al. |
| 6,241,725 | B1 | | 6/2001 | Cosman |
| 6,358,246 | B1 | | 3/2002 | Behl et al. |
| 6,379,353 | B1 | | 4/2002 | Nichols |
| 6,470,218 | B1 | | 10/2002 | Behl |
| 6,471,695 | B1 | | 10/2002 | Behl |
| 6,475,226 | B1 | * | 11/2002 | Belef et al. .................... 606/185 |
| 6,685,700 | B2 | | 2/2004 | Behl et al. |
| 6,690,976 | B2 | | 2/2004 | Fenn et al. |
| 6,802,839 | B2 | | 10/2004 | Behl |
| 7,182,761 | B2 | | 2/2007 | Garabedian et al. |
| 7,416,549 | B2 | | 8/2008 | Young et al. |
| 7,458,971 | B2 | | 12/2008 | Zerfas et al. |
| 2002/0072742 | A1 | | 6/2002 | Schaefer |
| 2003/0152517 | A1 | | 8/2003 | Peyman |
| 2004/0044385 | A1 | * | 3/2004 | Fenn et al. .................... 607/100 |

FOREIGN PATENT DOCUMENTS

| WO | WO 99/00144 | 1/1999 |
| WO | WO-99/00144 | 1/1999 |
| WO | WO-03/070298 | 8/2003 |
| WO | WO 03/070298 A2 | 8/2003 |

(Continued)

OTHER PUBLICATIONS

John N. Weinstein et al, "Treatment of Solid L1210 Murine Tumors with Local Hyperthermia and Temperature-sensitive Liposomes Containing Methotrexate", Cancer Research 40, 1388-1395, May 1980.

(Continued)

*Primary Examiner* — Janet Epps-Smith

(74) *Attorney, Agent, or Firm* — Merek, Blackmon & Voorhees, LLC

(57) ABSTRACT

An apparatus and method for administering focused energy to a body using either a single energy applicator or multiple energy applicators to supply heat prior to, concurrently with and/or after delivery of a drug, gene and/or viral vector. A multi-modality treatment using a localized, focused and/or regional heating apparatus, which supplies heat to a defined area of a patient's body. The apparatus is used heat is used to pretreat a specific body site, to activate thermoactivated drugs, genes, or viral vectors, and/or to deliver drugs, genes, or viral vectors to the specific body site. The heating apparatus is provided with one or more variable and adjustable probes and one or more delivery ports heat the specific treatment site and to deliver the thermoactivated drugs and genes to the specific treatment site. Each probe may optionally be provided with one or more temperature sensors to allow for the temperature in the specific treatment site and the surrounding tissue to be properly regulated. The use of the apparatus and method allow for the heat conditioning of a specific treatment site and for the delivery or activation of a drug, gene, or viral vector limited to only the specific treatment site, allowing for a more accurate treatment of diseased tissue without damaging healthy tissue. In addition, this method is uniquely used with non invasive technologies to help determine on a real time basis the completion of the treatment.

30 Claims, 13 Drawing Sheets

(56) References Cited

FOREIGN PATENT DOCUMENTS

| WO | WO 2004/022159 A1 | 3/2004 |
| WO | WO 2005/007000 A1 | 1/2005 |
| WO | WO 2005007000 A1 * | 1/2005 |
| WO | WO-2006/102471 | 9/2006 |
| WO | WO 2006/102471 A2 | 9/2006 |

OTHER PUBLICATIONS

*Notification Concerning Transmittal of International Preliminary Report on Patentability* dated Oct. 4, 2007 issued in corresponding PCT patent application No. PCT/US2006/010505 together with the Written Opinion of the International Searching Authority and the International Search Report.

*Notification of Transmittal of the International Search Report and the Written Opinion of the International Searching Authority, or the Declaration* (together with the International Search Report and the Written Opinion of the International Searching Authority) dated May 14, 2007 issued in corresponding PCT patent application No. PCT/US2006/037569.

John N. Weinstein, et al. "*Treatment of Solid L-1210 Murine Tumors with Local Hyperthermia and Temperature-sensitive Liposomes Containing Methotrexate*," Cancer Research, vol. 40, No. 5, 1980, pp. 1388-1395, XP002429634.

* cited by examiner

DYNAMIC CONTROL OF HEAT W/RIGID TEMPERATURE FORMULATION RELEASE/ACTIVATED DRUGS AND/OR GENES AND/OR VIRAL VECTORS

DYNAMIC AND/OR STATIC AND/OR STEADY STATE HEATING PROFILE WITH BROAD TEMPERATURE
FORMULATION RELEASE/ACTIVATION DRUGS AND/OR GENES AND/OR VIRAL VECTORS

APPARATUS AND METHOD FOR PRE-CONDITIONING/FIXATION AND TREATMENT OF DISEASE WITH HEAT ACTIVATION/RELEASE WITH THERMOACTIVATED DRUGS AND GENE PRODUCTS

CROSS-REFERENCE TO RELATED APPLICATIONS

This application claims the benefit of priority of U.S. Provisional Application No. 60/664,699, filed on Mar. 24, 2005, the subject matter of which is incorporated herein by reference.

BACKGROUND OF THE INVENTION

1. Field of the Invention

The present invention generally relates to an apparatus and method for administering a focused energy treatment to a limited, defined area of a patient's body. The energy treatment is delivered by the use of one or more energy applicators. The energy applicators can be used to release and/or activate thermoactivated drugs and genes for the treatment of both cancerous, precancerous, and benign lesions as well as infectious diseases.

In particular, the present invention relates to a multi-modality treatment employing a localized, focused and regional heating apparatus to treat and/or pretreat a specific body site and to release/activate thermoactivated drugs and genes at the specific body site by using heat. The present invention relates to a heating apparatus and a method of using the same. The apparatus includes one or more energy applicators designed to uniquely provide one or more delivery ports, which deliver the thermoactivated drugs and genes to the specific treatment site. In addition, the applied heat energy may be used to precondition and/or condition the targeted treatment site and also to uniquely cause the fixation and localization of both the release and/or activation of the thermoactivated drugs, genes, or viral vector to the specific treatment site based upon the unique thermo-boundaries formed by the use of heat either before, concurrently, and/or after the delivery of the drug, gene and/or viral vector. As a result, the invention can limit and/or increase the targeted treatment site and minimize the impact on normal cells.

2. Description of the Prior Art

In order to treat a specific treatment site, such as liver lesions, prostate, breast, head and neck, bone, lungs, brain, pancreas, kidney, thyroid or other localized solid or defused neoplasms, doctors have used focused heating devices such as Radio Frequency Ablation (RFA), Microwave Ablation (MA), Laser Ablation (LA), Ultrasound Ablation (UA), High Intensity Focused Ultrasound (HIFU), and focused microwaves (FM) used as a single modality. The previous uses of these treatments were limited in focus and to small effective treatment regions. Recurrent tumors often occur at the margins of a previously treated tumor. There may be ineffective cold spots throughout the treatment zone due to the non-homogeneous nature of these previous heating methods. The use of modalities such as RFA can indeed effectively heat a small defined area of tissue, but this small defined area is limited to tissue in close proximity to a deployed heating antenna. This limited area is usually only within 1 to 2 centimeters of the deployed heating antenna, and this limited area suffers from non-homogeneous heating due to blood flow, tissue impedance, and other types of energy sources. Past uses of prior heat treating apparatuses have resulted in unsatisfactory tumor control, generally limited to the immediate center of the treatment site. As a consequence, significant tumor recurrence and/or continued growth of the cancerous tumors are common. Accordingly, there is a major need to increase the therapeutic kill zone of single heat modalities currently employed.

One of the major uses for the above-described heating devices is for the treatment of hepatocellular carcinoma (HCC). Hepatic tumors are either primary or secondary (i.e. metastatic liver cancer or MLC) and are a substantial medical problem both in the United States and worldwide. The worldwide annual mortality as a result of HCC is estimated annually to be approximately 1,000,000 persons.

Generally, chemotherapy and radiation therapy are ineffective for treatment of hepatic tumors and certain localized tumors where the above heating modalities are used. The gold standard for the treatment of liver tumors and many solid localized tumors is the surgical resection of the tumor. Unfortunately, less than 20% of patients of primary or secondary liver tumors are eligible for surgical resection due to size limitations. This is also the case where solid tumors have advanced in size, such that it may not be safe to remove the tumor from the organ without compromising the well being of the patient. Even with surgical resection, 5 year survival rates are less than 30%. The outlook is even grimmer for patients with unresectable hepatic tumors. Thus, there is a major need for a more effective treatment option for both resectable and unresectable tumors.

Radio-Frequency ablation (RFA) for the treatment of liver cancer was first investigated in the early 1990's. Since that time RFA has quickly become one of the most used minimally invasive treatments for HCC and MLC. There are numerous RFA devices commercially available worldwide to create the thermal lesions that ablate the cancer cells. The three primary RFA devices ultilized in the USA are RITA Medical Systems, Mountain View, Calif.; Radiotherapeutics, Mountain View, Calif.; and Radionics, Burlington, Mass. The power sources of the three devices are very similar in usage, except that the actual RFA heating probes used to deliver heat are different. Both the RITA Medical Systems and the Radiotherapeutics devices have an umbrella or "Christmas tree" configuration while the Radionics device uses a cool tip single or multiple needle design. The RITA Medical Systems device uses a temperature feedback control whereas the other two employ an impedance feedback control to terminate the treatment. The clinical applications placing the RFA probes in the proximity of the tumor can be performed either by open surgery or laproscopically, generally administered by a surgeon, or a less invasive procedure such as percutaneous which is generally administered by interventional radiologists.

However, regardless of which RFA probes are used or which method of clinical application is used, the RFA treatments are best suited for smaller lesions less than 3 cm in diameter. Thus, all of the devices have similar limitations in the ability to effectively treat larger lesions, especially viable cancer cells in the margins. The "margins" are defined by the area outside the solid tumor. The margins outside the boundary area of the tumor in most cases could be up to 2 cm in width. It is desirable to attempt to create tumor free margins or boundaries beyond the imaged tumor lesion of 1 cm or greater; however, RFA is often limited in its ability to produce such consistent margins especially for tumors greater than 3 cm in their maximal diameter. The result is that viable tumor cells are left within such margins or the area between overlapping ablation zones where tissue is heated above 40 degrees C., but temperatures are not achieved within the necessary thermal ablation range (e.g., generally greater than 50 degrees C.).

As a result, known RFA devices are very limited to areas which can be effectively heated to high enough temperatures, generally greater than 50 degrees C. and targeted to be greater than 80 degrees C., in order to ablate the viable cancer. The high temperature requirement presents difficulties in preventing damage to surrounding non-cancerous tissues. Known high temperature ablative devices have had very limited success because it is difficult to heat the cancer cells at the margins to greater than 50 degrees C. to kill the diseased tissue and still prevent significant damage to the surrounding non-cancerous tissue.

High-energy Intensity Focused Ultrasound (HIFU) is another focused heating device. HIFU directs ultrasound to a focused region in order to significantly increase the temperature to kill and/or ablate diseased tissue in the targeted region. HIFU uses ultrasound thousands of times more powerful than the ultrasound used for imaging. Several HIFU systems are clinically available (Ablatherm from EDAP-Technomed, Lyon France and Sonablate from Focus Surgery, Indianapolis, Ind.) as well as several systems under development in China, Europe, and the USA. Treatment applications have included localized prostate cancer, liver cancer, and benign breast and uterine tumors. With regards to the treatment of prostate tumors, these systems may be less invasive than surgery, cyroblation, and seed implants, which have potentially greater adverse events or effects, but the use of HIFU has also been associated with adverse events, such as incontinence, recto-urethral fistulas, edema, and chronic necrotic debris and infection. In addition, due to limitations on the size of treatment zone, the complete control rate will be very difficult to achieve with these known systems. HIFU has also been used for other localized cancers with marginal success due to difficulty of use, limited size of ablation area, and difficulty of focusing and directing the energy to exactly where it is required.

Other technologies, such as lasers as developed by Indigo and Johnson & Johnson, transurethal incision of the prostate (TULIP), and visual laser ablation (VLAP), have similar limitations and clinical shortcomings as those of RFA. These shortcomings include the limited size of the effective targeted area generated by these technologies and potential adverse events caused by the high intensity heat. The inability to see in real time the amount of heat generated and the actual location of where the high heat is generated can also pose a problem and lead to significant cell death in the adjacent normal (healthy) cells. The major shortcomings include not only the non-uniformity within the targeted treatment zone but also the shortcomings of effective heating zones at the margins of the lesions or tumors.

Microwave ablation (MA) probes have been used to deliver heat to lesions or tumors, but this technology is invasive. This technology is very similar to the usage of RFA technologies. To some extent, MA may be limited by the problem of heat sinks around/near blood vessels thereby resulting in cool spots that are not heated to a sufficient temperature to treat and/or kill the lesion or tumor. Another potential limitation is that MA can take longer to heat a very confined area of lesion or tumor tissue.

Drug therapy is a standard of care (SOC) for the treatment of many cancerous and infectious diseases. The goal of drug therapy is to be able to deliver an adequate dose of a drug to the specific organ or site to be treated without damaging or killing normal cells. Cytotoxic drugs for the treatment of disease are generally delivered systemically and thus are non-site specific nor cell-specific. As a result, the delivery of cytotoxic drugs can become very toxic to normal cells and vital organs. Several new drugs have been designed to specifically target the cancer by binding to tumor cell specific antigens. These drugs must typically be very potent to be effective and can kill tumor cells within a specific cancer indication carrying the necessary cell surface receptors. Further, due to physical limitations, blood flow, physiological limitations, higher and more effective doses of anti-cancer agents are generally not achievable. Consequently, for many localized lesions within organs such as the liver, prostate, lung and breast, complete disease site control including the tumor margins has not been significantly improved nor is there a dramatic increase in survival rates.

In some cases, such as with treatment for the prostate gland, the goal is to provide an effective treatment to the diseased region within the gland, without causing major adverse events such as incontinence, sterility, pain, impotency and also retrograde ejaculation. These adverse events are also a byproduct of surgery, external radiation and implant therapy, cyrotherapy, and RFA. Even with thermotherapy, it is necessary to heat a significant portion of the prostate gland while sparing healthy tissues in the prostate as well as the surrounding tissues including the urethral and rectal walls of a patient. Thus, cancer cells in the margins again are not effectively treated. The prostate gland encircles the urethra immediately below the bladder. The prostate, which is the most frequently diseased of all internal organs, not only is a site of a common affliction with cancer among older men, but also for benign prostatic hyperplasia (BPH) and acute prostatitis. Recent treatment of BPH includes transurethral microwave thermotherapy in which microwave energy is employed to elevate the temperature of tissue surrounding the prostatic urethra above about 45° C., thereby thermally damaging the tumorous prostate tissue. U.S. Pat. Nos. 5,330,518 and 5,843,144 describe methods of ablating prostate tumorous tissue by transurethral thermotherapy. There remains a need to better treat diseased tissue to increase the survival rate of patients and decrease the adverse side effects of treatment.

SUMMARY OF THE INVENTION

The present invention relates to an apparatus and method for administering focused energy to a body using either a single energy applicator or multiple energy applicators to supply heat prior to, concurrently with and/or after delivery of a drug, gene and/or viral vector. A multi-modality treatment using a localized, focused and/or regional heating apparatus, which supplies heat to a defined area of a patient's body. The apparatus is used to heat or pretreat a specific body site, to activate thermoactivated drugs, genes, or viral vectors, and/or deliver drugs, genes, or viral vectors to the specific body site. The heating apparatus is provided with one or more variable and adjustable probes and one or more delivery ports to heat the specific treatment site and to deliver the thermoactivated drugs and genes to the specific treatment site. Each probe may optionally be provided with one or more temperature sensors to allow for the temperature in the specific treatment site and the surrounding tissue to be properly regulated. The use of the apparatus and method allow for the heat conditioning of a specific treatment site and for the delivery or activation of a drug, gene, or viral vector limited to only the specific treatment site, allowing for a more accurate treatment of diseased tissue without damaging healthy tissue.

Furthermore, the claimed apparatus according to the invention addresses the shortcoming mentioned above in that the apparatus provides one the ability to see in real time the amount of heat generated at a specific location and the actual location where the high heat is generated that can pose a problem and lead to significant cell death.

The method of the present invention includes the steps of determining the size and shape of a treatment area of diseased tissue, heating the treatment area to a desired temperature, using one or more temperature sensors to receive feedback about the temperature in the treatment area and in the surrounding healthy tissue, adjusting the heating of the treatment area to control the heating of the treatment area, the introduction of a thermoactivated drug, gene, or viral vector into the treatment area whereby the heat applied to the treatment area activates (or releases for thermoactivated release drugs, genes, or viral vectors) the drugs, genes, or viral vectors to allow for the treatment of the diseased tissue in the treatment area. The introduction of the heat is preferably applied by the use of one or more energy applicator, such as Radio Frequency Ablation (RFA), Microwave Ablation (MA), Laser Ablation (LA), Ultrasound Ablation (UA), High Intensity Focused Ultrasound (HIFU), and/or focused microwaves (FM). The drugs are introduced to the treatment area either by intravenous injection (I.V. or intra-arterial) into the patient (where the drugs are activated in the treatment area by the applied heat) or direct intratumoral injection into the treatment zone.

A further embodiment of the method according to the present invention is a method for the delivery of the heat so that the heat can be delivered to the site pre-delivery of the thermoactivated drugs, genes and/or viral vector to pre-condition or condition the targeted tissue to be treated and/or fixate the drugs, genes and/or viral vector to the targeted tissue to be treated. The step of introducing the heat initially releases, activates, enhances, and/or expresses delivery of thermoactivated drugs, genes and/or viral vector to the targeted tissue to be treated, and then these drugs, genes and/or viral vector will effect the targeted tissue to be more susceptible to heat damage at the targeted tissue to be treated.

In addition, another embodiment of the inventive method includes the delivery of the heat to the site simultaneously with the delivery of the thermoactivated drugs, genes and/or viral vector to the targeted tissue to be treated vector to pre-condition or condition the targeted tissue to be treated and/or fixate the drugs, genes and/or viral vector to the targeted tissue to be treated. The method for the delivery of the heat could also be delivered to the site post delivery of the thermoactivated drugs, genes and/or viral vector to the targeted tissue to be treated vector to pre-condition or condition the targeted tissue to be treated and/or fixate the drugs, genes and/or viral vector to the targeted tissue to be treated.

The above method could further be used with a method of dynamic control of heat to optimize the spatial delivery of a rigid temperature release thermoactivated drugs and/or genes and/or viral vector to the targeted tissue to be treated with the rigid temperature release as designed to release, activate and/or express the majority of the encapsulates within a designated narrow temperature tolerance (e.g. 2 to 3 degrees C.). In another embodiment, the use of the dynamic control of heat to optimize the spatial delivery of a broad range temperature release thermoactivated drugs and/or genes and/or viral vectors to the targeted tissue to be treated with the broad range temperature release is designed to release, activate and/or express the majority of the encapsulates within a 0-15 degrees C. tolerance. A preferred temperature range to release/activate drugs and/or genes and/or viral vectors is approximately 40 degrees C. through 55 degrees C. That is, when a rigid temperature release thermoactivated drug is employed, the drug may be designed to be released into the tissue and/or blood stream at tissue temperatures of 40 degrees C. to 42 degrees C., 39 degrees C. to 41 degrees C., or any other 2-3 degree temperature range within the preferred temperature range. Similarly, a broad range temperature release thermoactivated drug would be designed to be released when the tissue is heated to 40 degrees C. to 55 degrees C.

An additional method or use of the inventive apparatus or method is the use and control of a static and/or steady state heating profile to optimize the spatial delivery of a rigid temperature release thermoactivated drugs and/or genes and/or viral vectors to the targeted tissue to be treated. The rigid temperature release is designed to release, activate and/or express the majority of the encapsulates within a designated narrow temperature tolerance (e.g. 2 to 3 degrees C.). The method could also be used with the use and control of a static and/or steady state heating profile to optimize the spatial delivery of a broad range temperature release thermoactivated drugs and/or genes and/or viral vector to the targeted tissue to be treated. The broad range temperature release is designed to release, activate and/or express the majority of the encapsulates within a 0-15 degrees C. tolerance. A preferred temperature range to release/activate drugs and/or genes and/or viral vectors is approximately 40 degrees C. through 55 degrees C.

Embodiments of the method according to the invention include the delivery of the heat to the site pre-delivery, simultaneously and/or post delivery of the thermoactivated drugs and/or genes and/or viral vector to pre-condition or condition the targeted tissue to be treated and/or fixate the drugs, genes and/or viral vector to the targeted tissue to be treated. In addition, this method could be used with the control and use of either static or dynamic control of heat in addition, with broad or rigid range temperature dependent upon the carriers of drugs, genes, and/or viruses.

Furthermore, the method of this invention allows for a usage of the targeted tissue to be treated and also a method to optimize the treatment. This method uses either a single heating profile or combinations of various heating profiles of the various technologies which could be used either by controlling the dynamic heating profiles or the static steady states profiles of each heating technology. In addition, this method is further optimized in use with specifically designed release and activation properties of broad temperature range within a 0-15 degrees C. tolerance. Thus, a preferred temperature range to release/activate drugs and/or genes and/or viral vectors is approximately 40 degrees C. through 55 degrees C. In addition, this method is further optimized in use with specifically designed release and activation properties of rigid temperature range within a 1-2 degrees C. tolerance. Thus, any narrow tolerance within the preferred temperature range could be used to release and/or activation drugs/genes or viral vectors to the targeted tissue.

Furthermore, this method addresses the shortcoming in the inability to see in real time the amount of heat generated and the actual location of where the high heat is generated can also pose a problem and lead to significant cell death. This leads to the inability to determine when the preconditioning, treatment, release, activation and/or fixation is completed. The above method could then be combined with other technologies such as non invasive approaches such as realtime MRI, ultrasound, CT, laser, infrared, PET, and/or other imaging technologies to complete the desired results. In addition, another embodiment of the method would employ the use of microwave or RF radiometer technologies to also determine completion of the desired results.

The apparatus of the present invention is a device that includes a catheter, at least one probe, a control unit, and conduits for transferring liquids and gasses, for transferring energy, and for transferring temperature readings. There is preferably a plurality of probes each including at least one of a temperature sensor, a fluid or gas port, and an energy emitter. In the preferred embodiment, each probe includes a plurality of temperature sensors, fluid or gas ports, and energy emitters. Some embodiments may have probes that include energy emitters alone or energy emitters with temperature sensors and fluid ports or temperature sensors and other proves with energy emitters. The temperature sensors are used to read the temperature in different sections of the treatment zone to allow for the heating of the treatment zone and to control the heating process to ensure that the treatment zone remains at the desired temperature and that the surrounding healthy tissue around the treatment zone does not become heated. The fluid and gas ports are used for direct intratumoral injection of a thermoactivated drug, gene, or viral vector into the treatment zone. These ports may also be used to deliver cooling liquid or gas into the treatment zone. The energy emitters deliver an energy source to the treatment zone that heats the diseased tissue in the treatment zone to the desired temperature. The desired temperature is below the normal abatement temperature so that surrounding tissue is not damaged by the heating of the diseased tissue, but is sufficient to activate the thermoactivated drugs, genes, or viral vectors introduced into the treatment zone. By using a lower heat level in combination with thermoactivated drugs, genes, or viral vectors, this device allows for the precise treatment of diseased tissue without significantly harming the surrounding healthy tissue. The design of the device allows for a user to fix and control the size and shape of a treatment zone, which allows for the exact treatment of only the diseased tissue (killing even the diseased tissue at the margins of the treatment area) while not damaging the surrounding healthy tissue.

BRIEF DESCRIPTION OF THE DRAWINGS

These and other features and advantages of the invention will be further understood from the following detailed description of the preferred embodiment with reference to the accompanying drawings in which.

DETAILED DESCRIPTION OF THE INVENTION

Figures 1, 1A:
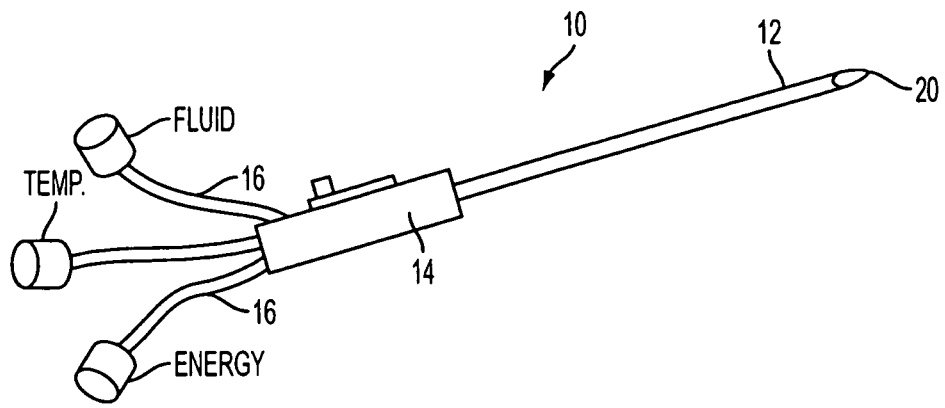
FIGS. 1A-1, 1A-2, and 1A-3 illustrate a variable extendable energy probe according to a first embodiment of the invention.

The present invention is directed to a device and a method for thermally treating tissue not only to the limited small focal zone generally well known as the effective therapeutic zone, but also used to expand this zone and boundary conditions by use of heat as a precondition, conditioning and a fixation method controllable to that of a desired targeted treatment area. This defined targeted treatment area, thus, enables the release and/or activation of thermoactivated drugs and genes for the treatment of both cancerous, precancerous, benign lesions as well as infectious diseases. Furthermore, according to this invention, this is a method of using heat to fixate the thermoactivated drugs, genes, and/or viral vector to the targeted tissue to be treated.

The present invention relates to an apparatus and method for administering focused energy to a body using one or more energy applicator, such as Radio Frequency Ablation (RFA), Microwave Ablation (MA), Laser Ablation (LA), Ultrasound Ablation (UA), High Intensity Focused Ultrasound (HIFU), and/or focused microwaves (FM), to release and/or activate thermoactivated drugs and/or genes for the treatment of both cancerous, precancerous, benign lesions as well as infectious and non infectious diseases. In particular, the present invention relates to a multi-modality treatment using a localized, focused and/or regional heating apparatus used to treat and pretreat a specific body site and is to be used to release or activate thermoactivated drugs and genes using heat.

The presently inventive method includes administering a preconditioning or conditioning energy to the target site (a defined area of diseased tissue in a patient's body) and the delivery of a drug, gene and/or viral vector to the target site. The size of this volumetric area is uniquely predetermined by achieving at least a predetermined target temperature within the targeted area and is extended to a predetermined boundary based on achieving a minimum target temperature over a period of time at the boundary. Thus, this invention allows the desired target area to be treated. As a result, the released drugs, genes, and/or viral vector will be preferentially delivered, released, absorbed, and/or activated at the desired target treatment area. Therefore, this invention can predetermine the size and boundaries of the desired treatment zone and can limit collateral damage to normal tissue. The use of this invention to pre-condition and/or condition will also be used to fix and limit the area of exposure of the drug, gene, and/or viral vector. Consequently, this invention improves upon the ability to perform a more complete tumor burden reduction, especially for larger lesions and at the margins of all lesions. Tumor burden as defined by viable cancer cells within a particular volumetric area in question.

The step of applying energy to the target area may include a single energy applicator or multiple energy applicators. The applied energy, preferably heat energy, provides fixation and localization of both the release and/or activation of the thermoactivated drugs and genes to the specific treatment site based upon the unique thermo-boundaries formed by the heat delivered to the target area. Consequently, this invention can effectively use the lower temperatures than the prior art heating methods, which damages surrounding healthy tissue, to activate and/or release drugs or genes with its unique delivery system of thermoactivated drugs or genes. The use of lower temperatures will thus prevent damage to the surrounding health tissue, but yet still treat the treatment site by releasing or activating the thermoactivated drugs, genes, or viral vectors. It is also possible that the step of applying energy could constitute the cooling of the target area to activate thermoactivated drugs that are activated when exposed to temperatures cooler than the ambient temperature of a human being. An example of a thermoactivated drug is the heat-sensitive or thermosensitive liposome described in U.S. Pat. No. 5,094,854, incorporated herein by reference.

In order to increase the effective treatment field, as well as to verify and confirm the size of the treatment field, this method uses both adjustable temperature sensors and multiple point sensors or independent sensors. The ability to deploy adjustable temperature sensors will allow verification of if adequate heating is limited to the desired distance from the heating probe. Thus, the adjustable temperature sensors of the present invention will also be used as a safety control the heating of the target site and the surrounding healthy tissue and thus not activate nor release drugs and/or genes in normal healthy tissues. The ability to adjust and either expand or retract the heating probes of the invention enables one to custom heat the desired volumetric heating zone without the need to develop different fixed-sized heating probes for each desired heating zone. The clinical outcome is to provide and deliver a larger kill zone of the lesion or tumor (targeted site), which overcomes clinical limitations of known heat energy systems. The uniqueness of this invention can predetermine the size, shape and effective therapeutic zone with the preheating or concurrent-heating to be able to fixate the therapeutic zone to a targeted area for the release/activation of thermoactivated drugs and/or genes delivery.

The thermoactivated and/or released drugs and/or genes can be delivered by intravenous injection (I.V.), intra-arterial or direct intratumoral injection in order to deliver a drug, gene, viral vector, or medicine to a targeted region. To achieve this object, the instant method may employ the various focused heating devices such as Radio Frequency Ablation (RFA), Microwave Ablation (MA), Laser Ablation (LA), Ultrasound Ablation (UA), High Intensity Focused Ultrasound (HIFU), and focused microwaves (FM) as the minimally invasive or non-invasive energy-emitting source. However, in the case of RFA, the present invention may be used as it relates to the heating apparatus in the use of the single and or multiple energy applicators to uniquely provide delivery port(s) to deliver the thermoactivated drugs and genes to the specific treatment site. In addition, the applied heat energy of the present invention also provides for the fixation and localization of both the release and activation of the thermoactivated drugs and/or genes to the specific treatment site based upon the unique thermo-boundaries formed by the use of the apparatus described herein.

This instant method could use the delivery apparatus to only deliver energy to the target area and use intravenous injection (I.V. or intra-arterial administration) rather than direct intratumoral injection of the drug, gene or medicine to a specific targeted region, or simply use the device for intratumoral injection of drugs, genes, or viral vectors into the target area with the use of a different means to apply energy to the targeted region, or use the device to perform both steps. The preferred embodiment is to use the device to preheat (precondition) the target area, then continue heating the target area in combination with introducing thermoactivated and/or released drugs, genes, and/or viral vectors by direct injection into the target site through the device. This method may also be suitable for use with drugs that are effective at the human ambient body temperature, but increase in activity at a different temperature. Thus, unlike known ablative techniques of the prior device, the instant invention may use low temperatures that are significantly below the generally accepted therapeutic ablative temperatures of greater than 50 degrees C. when combined with thermoactivated and/or released drugs and/or genes in order to increase the effective targeted treatment zone currently not achievable with conventional ablation techniques.

The method will heat the target area of a temperature optimal for preventing damage to the surrounding healthy tissue while also sufficiently activating thermoactivated drugs, genes, or viral vectors. The preferred heating range will depend upon the specific thermoactivated drug used, but the preferred method uses a temperature less than 50 degrees C., preferably about 39-41 degrees C. An example of a thermoactivated drug is the heat-sensitive or thermosensitive liposome described in U.S. Pat. No. 5,094,854, incorporated herein by reference. The preferred temperature for activation of this liposome is approximately 41° C., but a lower temperature activation can be realized.

The Applicant believes that the both the use of energy focused heating devices, such as Radio Frequency Ablation (RFA), Microwave Ablation (MA), Laser Ablation (LA), Ultrasound Ablation (UA), High Intensity Focused Ultrasound (HIFU), and focused microwaves (FM) to achieve a minimally invasive or non-invasive approach for the energy-emitting source in combination with thermoactivated and/or released drugs and/or genes will be adequate to fulfill the clinical needs of optimizing the treatment of lesions an tumors to address the margins.

The applicant believes that the new inventive methods and use may optimize the treatment to the target tissue and address the short comings of current treatment technologies. Another method for the delivery of the heat could delivered the heat to the site prior to the delivery of the thermoactivated drugs, genes and/or viral vector to pre-condition or condition the targeted tissue to be treated and/or fixate the drugs, genes and/or viral vector to the targeted tissue to be treated.

In addition, the method for the delivery of the heat could be delivered to the site simultaneously with the delivery of the thermoactivated drugs, genes and/or viral vector to the targeted tissue to be treated vector to pre-condition or condition the targeted tissue to be treated and/or fixate the drugs, genes and/or viral vector to the targeted tissue to be treated. The method for the delivery of the heat could also be delivered to the site post delivery of the thermoactivated drugs, genes and/or viral vector to the targeted tissue to be treated vector to pre-condition or condition the targeted tissue to be treated and/or fixate the drugs, genes and/or viral vector to the targeted tissue to be treated.

The above method of delivering heat could be used with a method of the dynamic control of heat to optimize the spatial delivery of a rigid temperature release thermoactivated drugs and/or genes and/or viral vector to the targeted tissue to be treated with the rigid temperature release as designed to release, activate and/or express the majority of the encapsulates within a designated narrow temperature tolerance (e.g. 2 to 3 degrees C.). Further, a dynamic control of heat may be used to optimize the spatial delivery of a broad range temperature release thermoactivated drugs and/or genes and/or viral vector to the targeted tissue to be treated with the broad range temperature release as designed to release, activate and/or express the majority of the encapsulates within a 0-15 degree C. tolerance or range. A preferred temperature range of use is approximately 40 degrees C. through 55 degrees C. That is, when a rigid temperature release thermoactivated drug is employed, the drug may be designed to be released into the tissue and/or blood stream at tissue temperatures of 40 degrees C. to 42 degrees C., 39 degrees C. to 41 degrees C., or any other 2-3 degree temperature range within the preferred temperature range. Similarly, a broad range temperature release thermoactivated drug would be designed to be released when the tissue is heated to 40 degrees C. to 55 degrees C.

An additional method of use for this invention is the use and control of a static and/or steady state heating profile to optimize the spatial delivery of a rigid temperature release thermoactivated drugs and/or genes and/or viral vector to the targeted tissue to be treated. The rigid temperature release is designed to release, activate and/or express the majority of the encapsulates within a designated narrow temperature tolerance (e.g. 2 to 3 degrees C.). The method could also be used with the use and control of a static and/or steady state heating profile to optimize the spatial delivery of a broad range temperature release thermoactivated drugs and/or genes and/or viral vector to the targeted tissue to be treated. The broad range temperature release is design to release, activate and/or express the majority of the encapsulates within a 0-15 degrees C. tolerance. A preferred temperature range of the heated tissue is approximately 40 degrees C. through 55 degrees C. in which the thermoactivated drugs and/or genes and/or viral vector is designed to be released, activated and/or expressed to work or pre-condition the tissue to be treated.

Thus, the method according to the invention, the delivery of the heat could be delivered to the site pre-delivery, simultaneously and/or post delivery of the thermoactivated drugs and/or genes and/or viral vector to pre-condition or condition the targeted tissue to be treated and/or fixate the drugs, genes and/or viral vector to the targeted tissue to be treated. In addition, this method could be used with the control and use of either static or dynamic control of heat with either broad or rigid range temperature dependent carriers of drugs, genes, and/or viruses.

Furthermore, the method of this invention allows for the usage to the targeted tissue to be treated and also a method to optimize the treatment. This method uses either an independent heating profile or the combinations of various heating profiles of the various technologies which could be used either by controlling the dynamic heating profiles or the static steady states profiles of each heating technology. In addition, this method is further optimized in use with specifically designed release and activation properties of a broad temperature range within a 0-15 degree C. tolerance or range. Thus, a preferred temperature range is approximately 40 degrees C. through 55 degrees C. to release and/or activation drugs/genes or viral vectors to the targeted tissue. In addition, this method is further optimized in use with specifically designed release and activation properties of rigid temperature range within a 1-2 degrees C. tolerance. Thus, the range of the temperatures depends upon whether a rigid temperature release or a broad temperature release is being used and a preferred temperature range of the tissue to be treated of is approximately 40 degrees C. through 55 degrees C. to release and/or activation drugs/genes or viral vectors to the targeted tissue.

A feature of the inventive heating apparatus in the both single or multiple energy applicators is to provide one or more unique delivery ports to deliver the thermoactivated drugs and genes to the specific treatment site thereby enabling the inventive heating device to effectively operate a lower temperature. As explained above, the applied heat energy is used for the fixation and localization of both the release and activation of the thermoactivated drugs and genes to a specific treatment site based upon the unique thermo-boundaries formed by pretreatment heating or concurrent heating with the delivery of the thermoactivated drugs and/or genes. In order to increase the effective treatment field as well as to verify and confirm the size and shape of the treatment field, both adjustable temperature sensors and multiple point sensors or independent sensors may be disposed on an appendage(s) of the heating device. The ability to deploy adjustable temperature sensors will allow verification if adequate heating is limited to the desired distance from the heating probe. As a result, the present invention could be used as a single modality, which preheats or preconditions or concurrently heats the desired area to be treated in combination with thermoactivated or released drugs, genes, or viral vectors delivered by intravenous injection (I.V. or intra arterial) and or direct intratumoral injection by another device.

According to a preferred embodiment of the invention, a preheating or preconditioning period of the targeted treatment zone may be performed by starting the heating by the energy emitting device for a period of approximately up to 10 minutes prior to the administration of the drugs, genes and/or medicine or can be performed in combination with and/or concurrently at the same starting time for both. In addition, a cool down period may be used to fixate the drugs, genes and/or medicine to the targeted treatment zone. This may be accomplished by cooled air, gas, fluid or other lower temperature medium inserted via the fluid ports that could be used to also dispense the drugs, genes, and/or medicine to the targeted area. For example, a movable energy-emitting source (e.g., microwave antenna) having a variable length may have multiple accesses or openings along its variable length so that a liquid or gas drug, gene, or viral vector can exit the ports at different locations depending on the size and shape of desired treatment zone.

In the same manner, a temperature sensor could also be disposed along a variable length of a probe extending from the energy emitting device and/or multi-temperature sensors may be disposed along the length to allow for a better thermo mapping model. An exemplary embodiment could use one feature, a combination of any two, and/or a combination of all three: the antenna or energy emitter, liquid/gas ports, or temperature probes. These probes can also have radio or sonar markings so that devices, such as x-ray, ultrasound, MRI or other imaging technologies, can verify the physical placement of the energy emitting device of the present invention. In the same manner, one would be able to also view or treat the targeted treatment field if the probes have radio or sonar markings. Thus, the present invention can work together with either individual multi-channel array emitters or single emitters opening up into multiple array probes for the different energy modalities i.e., Radio Frequency Ablation (RFA), Microwave Ablation (MA), Laser Ablation (LA), Ultrasound Ablation (UA), High Intensity Focused Ultrasound (HIFU), and focused microwaves (FM).

The temperature sensors that can be used to control the size of the preconditioned or conditioned treatment zone may be either invasive, minimally invasive and non-invasive. For the invasive or minimally invasive technologies, use of thermistors, thermocouples, and/or fiber optics could be used. Another approach is the use of non-invasive temperature monitoring and control approaches such as, ultrasound, microwave, infrared, laser, CT, and, Magnetic Resonance Imaging (MRI).

A method using heat creates a targeted and pre-conditioned treatment zone. The delivery of the heat could be delivered to the targeted site pre-delivery, simultaneously with delivery, and/or post delivery of the thermoactivated drugs and/or genes and/or viral vector in order to pre-condition, condition and/or fixate the targeted tissue to be treated. The method according to this invention is to fixate the thermoactivated drugs and/or genes and/or viral vector to the targeted tissue to be treated.

Therefore, this invention improves upon the ability to address the limitations of heat alone modalities of the desired targeted treatment area. This invention uniquely uses heat as a precondition, conditioning and a fixation method that is controllable to a desired targeted treatment area. As a result, the present invention overcomes the shortcomings of known ablation techniques and addresses the limitations of SOC drugs, genes and viral vectors by targeting a specific treatment site, delivering thermoactivated drugs, genes, or viral vectors to the specific treatment site, activating the drugs, genes, and/or viral vectors in the preconditioned targeted area and enhancing the effectiveness of the limited, standard delivery. Due to the preconditioning of the target area by using heat generated by the energy-emitting device, this invention has the ability to predetermine the size of the targeted treatment area and/or to increase the effective treatment zone achieved with heat alone techniques. Moreover, the combination of pre-conditioning using heat and delivery of drugs and/or genes effectively can treat a larger targeted area with lower heating temperatures. Thus, the present invention enhances the targeted delivery and activation of the thermoactivated drugs and/or genes and/or viral vector and SOC drugs and genes, and also increases the targeted treatment zone.

Figures 1, 1A, 2:
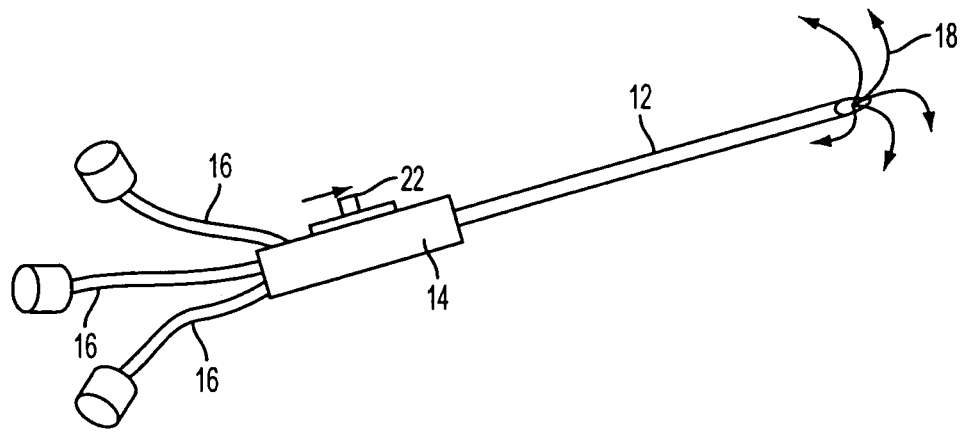
Figures 1, 1A, 2, 3:
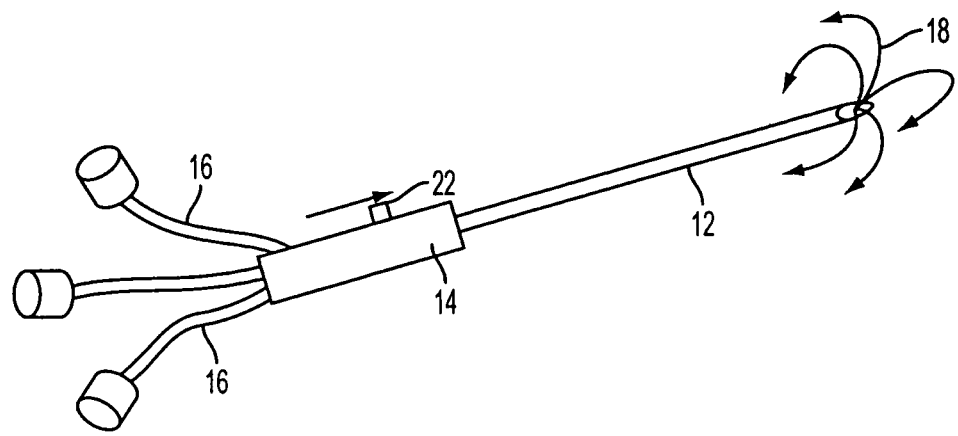

FIGS. 1A-1, 1A-2, and 1A-3 depict a preferred embodiment of the variable and adjustable probe device 10 used to treat diseased tissue. The device 10 includes a main catheter 12, which houses one or more probes 18. The lengths of the probes 18 are adjustable and variable. The catheter 12 is used to position the catheter port 20 at the catheter's tip into the general vicinity of a patient's diseased tissue (the treatment site), and the probes 18 are then extended out of the catheter port 20 to treat the diseased tissue. The catheter end that is not positioned within a patient's body is attached to a control unit 14, which allows for the control of the extension of the probes by the activation of switch 22. FIG. 1A-1 shows the probes 18 in a retracted position that allows for the catheter to be easily positioned within the patient's body. FIG. 1A-2 shows the probes 18 in a partially extended position caused by the partial activation of switch 22. FIG. 1A-3 shows the probes 18 in a fully extended position caused by the full activation of switch 22. The switch 22 may be any type of switch now known or later developed, including an electronic push button switch or a mechanical slide switch. The control unit 14 may include a plurality of switches 22 which each independently control one or more of the probes 18, which would allow for a user of the device 10 to create a variety of differently shaped treatment zones. The control unit 14 is connected to conduits 16 for transferring energy, fluid, and temperature information. To introduce a drug, gene, or viral vector through the device 10 directly to specific defined treatment area of diseased tissue in the patient's body, one would introduce the drug, gene, or viral vector through the fluid conduit 16. The fluid conduit 16 may also be used to introduce cooled air, gas, fluid or other lower temperature medium into the treatment area. One or more forms of energy are delivered to the treatment area through the energy conduit 16. Temperature readings from the treatment area are received through the temperature conduit 16. The control unit 14 may control the introduction of matter or energy into the patient's body.

Figure 1B:
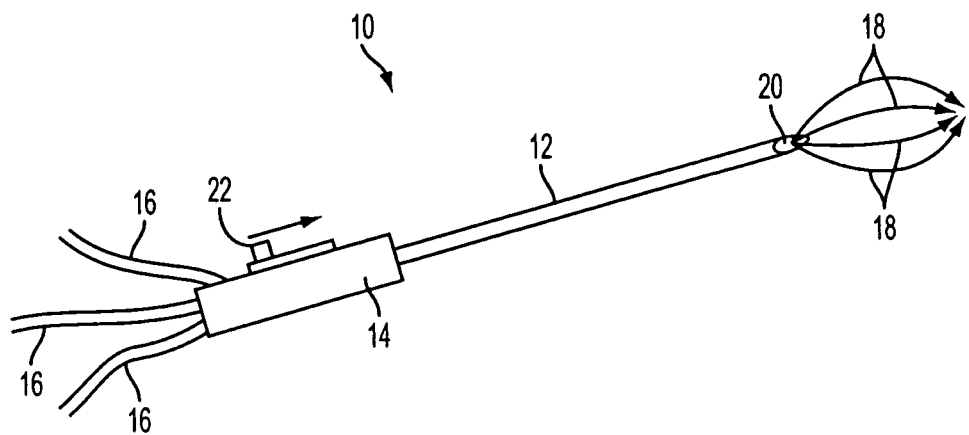
FIGS. 1B and 1C show another embodiment of a variable extendable energy probe according to the invention.
Figure 1C:
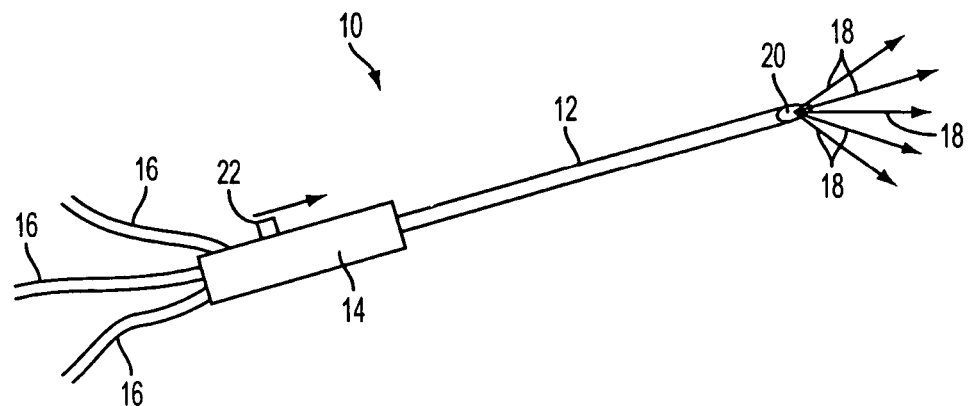

FIGS. 1A-2 and 1A-3 further show embodiments in which the probes 18 extend in a fish hook-like manner where the various probes twist back once they are extended out from the catheter port 20. The probes are formed such that they automatically come out in a fish hook-like array (J-shaped) once they are extended out of the catheter 12. The probes 18 of FIGS. 1A-1 through 1A-3 are variable extendable energy emitter. Depending upon the area to be treated, the probes 18 may be extended part way (FIG. 1A-2) or all the way out of the catheter port (FIG. 1A-3). FIG. 1B shows a second embodiment where the probes 18 form a bulging array (oval shaped) where the probes 18 exit the catheter port 20, at first diverging and then converging. FIG. 1C shows a third embodiment where the probes 18 form a linear array of probes diverging from a single point (the catheter port 20) in a linear fashion. These different embodiments of the probes 18 may be used to treat differently shaped and/or positioned treatment zones. The device 10 may be further designed to allow for the operator of the device 10 to select for the type of the probe array, as well as to select the degree of curvature of each probe by the use of the control unit 14. The device 10 may also allow for individual control of how each probe moves out of the catheter port 20, allowing for each individual probe 18 to be controlled for how far it is extended out of the catheter port 20, as well as for how each probe 18 curves.

Figure 2A:
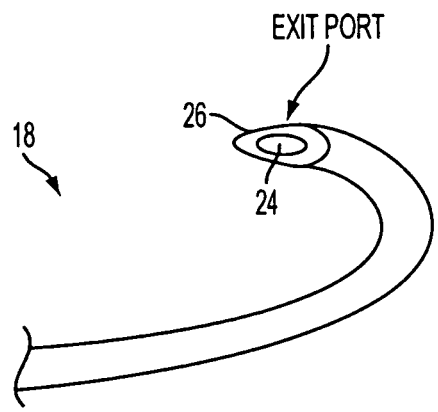
FIGS. 2A, 2B, and 2C are enlarged partial views of the extended probe showing a gas/drug/gene delivery exit port at the end of an extended probe.
Figure 2B:
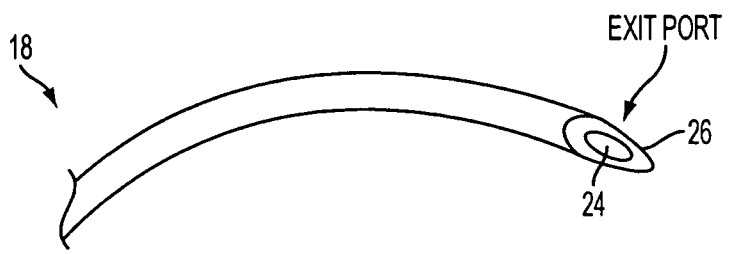
Figure 2C:
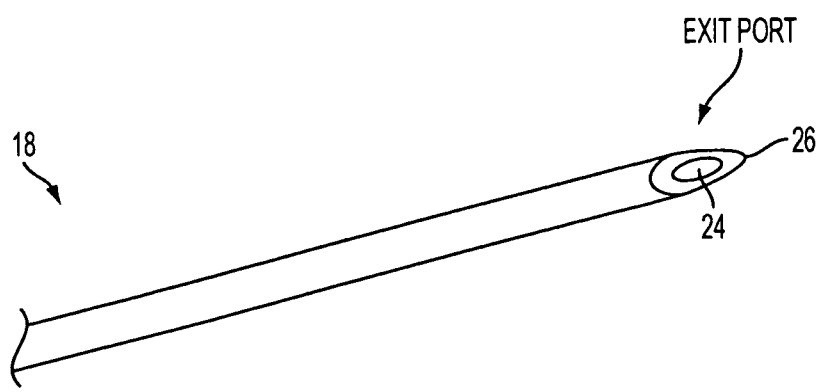
Figure 3A:
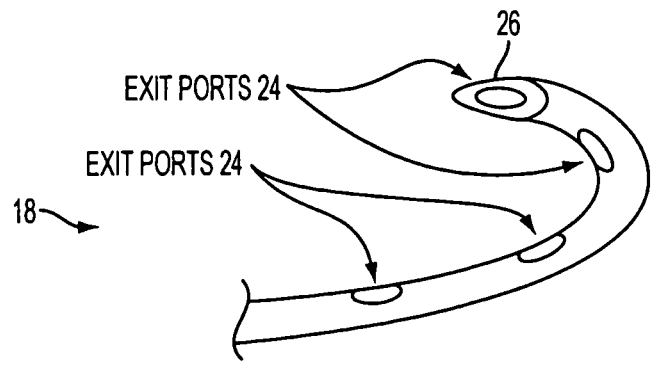
FIGS. 3A, 3B, and 3C show multiple delivery ports within one probe of an extended probe.
Figure 3B:
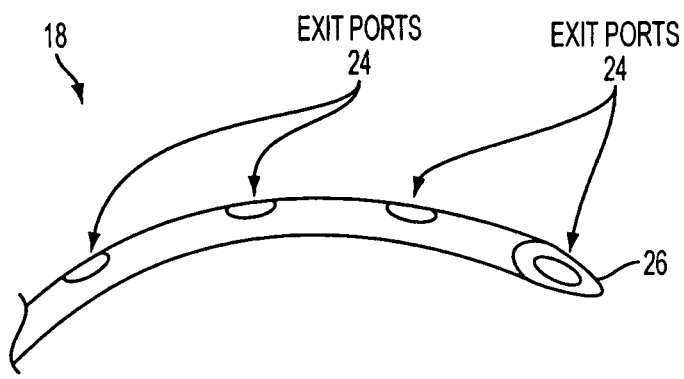
Figure 3C:
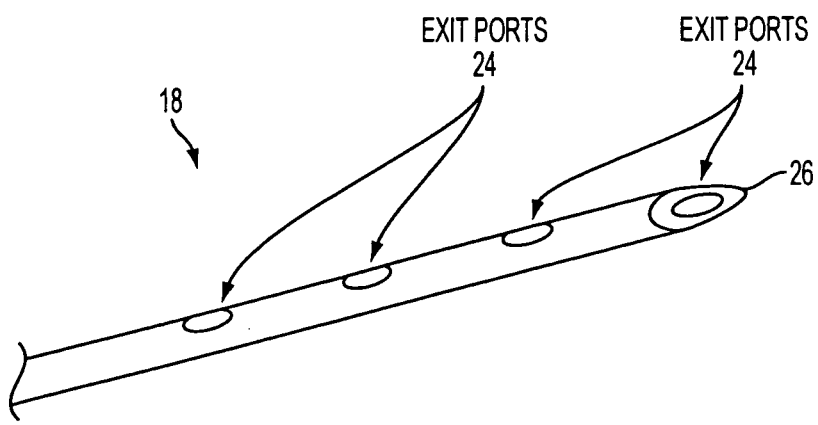

FIGS. 2A, 2B, and 2C show enlarged partial views of the extended probe 18 showing a gas/drug/gene delivery exit port at the end of an extended probe. These three figures show the probe in the different embodiments of probe arrays as discussed above. Each probe in this embodiment is provided with a single fluid port 24 at the tip 26 of the probe 18 for introducing the drug, gene, or viral vector to the treatment area. FIGS. 3A, 3B, and 3C show a second embodiment for providing probes 18 with fluid ports 24. Again, each of these figures show the probe in the different embodiments of probe arrays, as discussed above. Each probe in this embodiment includes multiple fluid ports 24 along the sides of the probe 18 as well as at the tip 26 of the probe 18. These fluid ports are in fluid connection with the fluid conduit 16 as shown in FIGS. 1A-1, 1A-2, and 1A-3, so that drugs, genes, viral vectors, or other fluid or gaseous media may be introduced into the treatment area of a patient's body through the device.

Figure 4A:
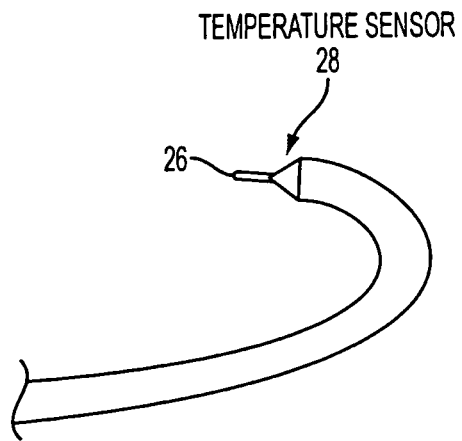
FIGS. 4A, 4B, and 4C are enlarged partial views of the extended probe showing a variable temperature sensor at the end of an extended probe.
Figure 4B:
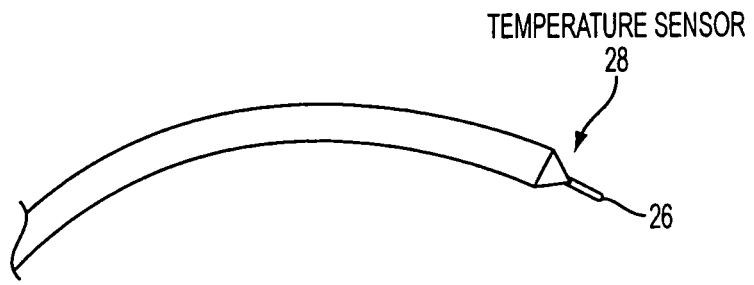
Figure 4C:
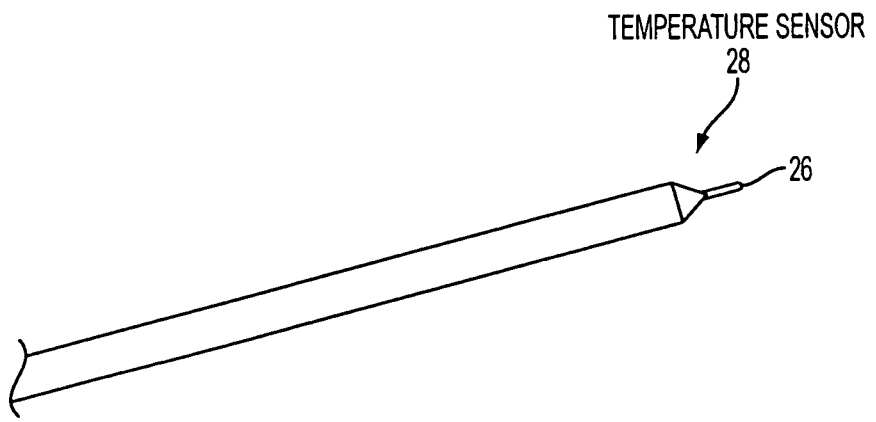
Figure 5A:
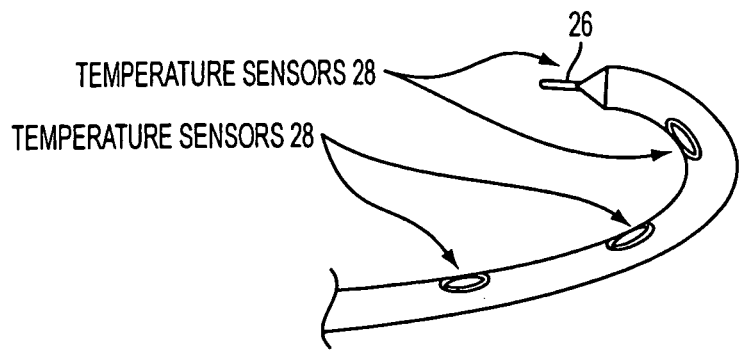
FIGS. 5A, 5B, and 5C are enlarged partial views of the extended probe showing multiple temperature multiple sensors disposed on an extended probe.
Figure 5B:
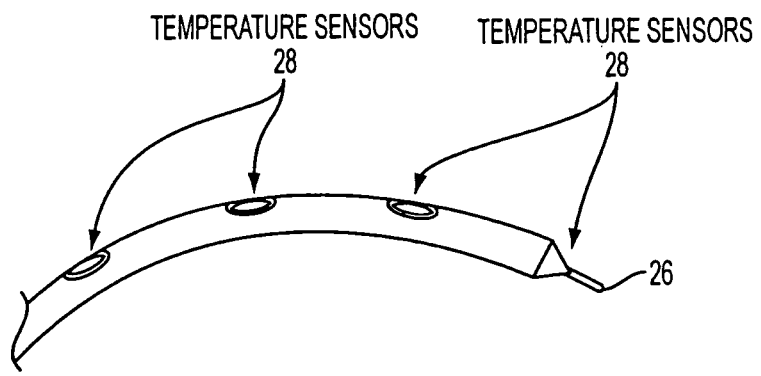
Figure 5C:
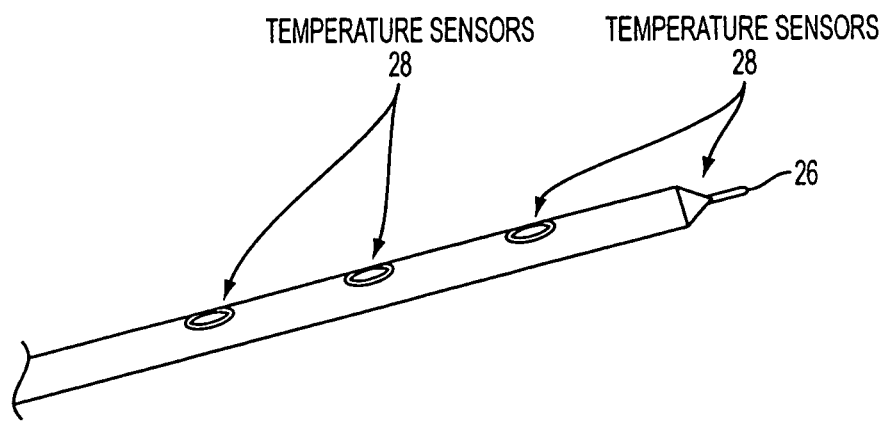

FIGS. 4A, 4B, 4C, 5A, 5B, and 5C show enlarged partial views of the extended probe 18 showing different embodiments having temperature sensors. FIGS. 4A, 4B, and 4C include a single temperature sensor 28 at the tip 26 of the probe 18. FIGS. 5A, 5B, and 5C include multiple temperature sensors 28 along the length of each probe 18 as well as at the tip 26 of each probe 18. These temperature sensors relay temperature reading information back through the temperature information conduit 16 so that the temperature information about the treatment location can be evaluated by a user of the device 10. The temperature information could also be analyzed by a device in the control unit 14 and displayed on the control unit 14. This information is used to adjust the amount and distribution of heat energy delivered to the treatment area so that the user of the device may ensure that only diseased tissue is treated while preventing damage to healthy tissue surrounding the treatment area.

Figure 6A:
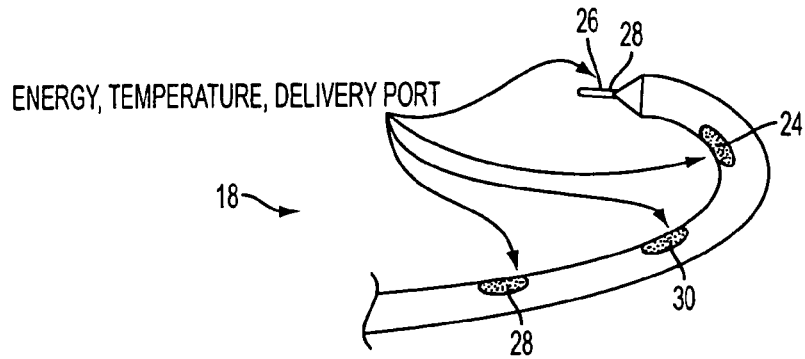
FIGS. 6A, 6B, and 6C are enlarged partial views of an extended probe with the multiple combinations of energy emitter, temperature sensor and delivery port disposed on an extended probe.
Figure 6B:
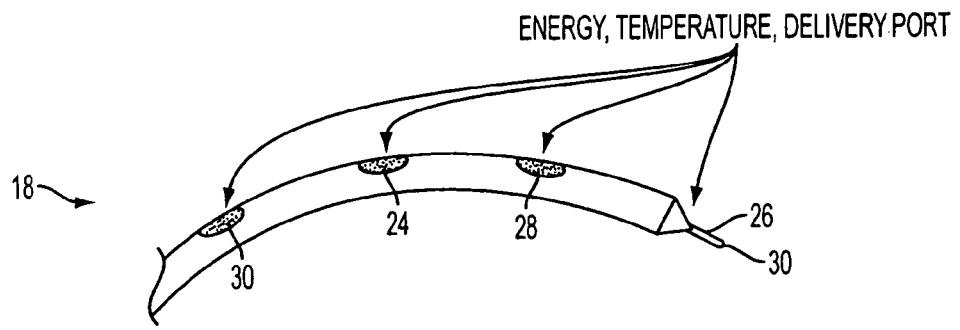
Figure 6C:
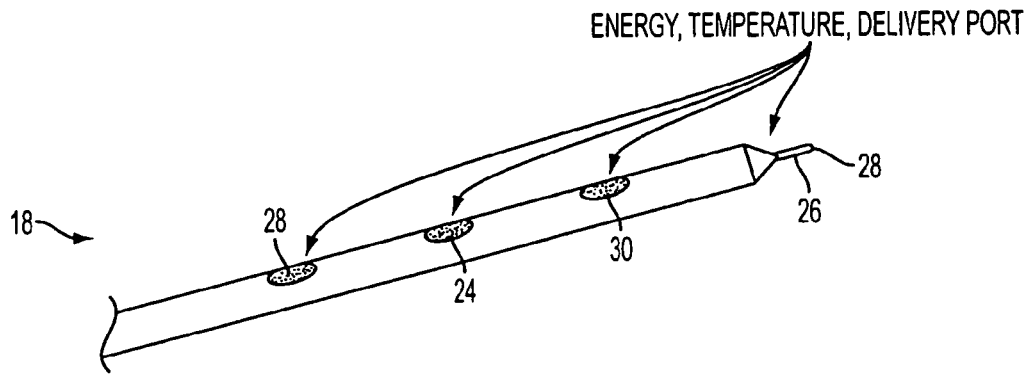

FIGS. 6A, 6B, and 6C show enlarged partial views of the extended probe 18 showing different embodiments having combinations of fluid delivery ports 24, temperature sensors 28, and energy delivery ports (energy emitters) 30. In this preferred embodiment, each probe has multiple temperature sensors 28, fluid delivery ports 24, and/or energy delivery ports (energy emitters) 30. With each probe having each of these types of sensors or ports would allow for the optimal level of treatment and control of the treatment of diseased tissue. The multiple energy ports (energy emitters) deliver heating energy to the diseased tissue so that the diseased tissue is preconditioned prior to the delivery of a drug, gene, or viral vector and to heat the treatment area during and/or after delivery of thermoactivated drugs, genes, or viral vectors to activate thermoactivated drugs, genes, or viral vectors. The heating devices delivers energy in the form of Radio Frequency Ablation (RFA), Microwave Ablation (MA), Laser Ablation (LA), Ultrasound Ablation (UA), High Intensity Focused Ultrasound (HIFU), focused microwaves (FM), or any other type of energy source as the minimally invasive or non-invasive energy. The device could also use these energy sources in combination. This heat is delivered to the treatment area through the energy ports (energy emitters) 30, through the probes 18 (which each travel through the catheter 12) through the control unit 14, through the energy conduit 16 from an initial energy emitting device delivering one or more of the above listed types of energy. Multiple energy conduits 16 would preferably be used if the device uses multiple types of energy forms to heat the treatment zone. The entire body of the probes 18 themselves may constitute an energy emitter 30, depending upon the type of energy delivery device used, but the energy emitters might also constitute ports for the delivery of energy prongs into the desired area of a patients body or for the transmission of energy waves to the desired area of a patient's body.

During the applications phase, a physical pulsing (turning on and off the energy source) may be used in the physical and mechanical caused by cell agitation to also aid in the activation and or release and absorption of the material applied to a patient via an intravenous or injection method. This application phase can also aid in the mechanical fixation of the drugs and or gene therapy compounds to the targeted protein and/or DNA tissue. It is noted that this mechanical method of fixation may cause the binding of the drugs and/or gene therapy compound disposed in the coated balloon to the protein and/or DNA. The resultant binding of the drug or gene therapy compound to the targeted protein and/or DNA is a major new innovation to ensure that the desired compound is effectively fixated or delivered to the targeted tissue.

Figure 7A:
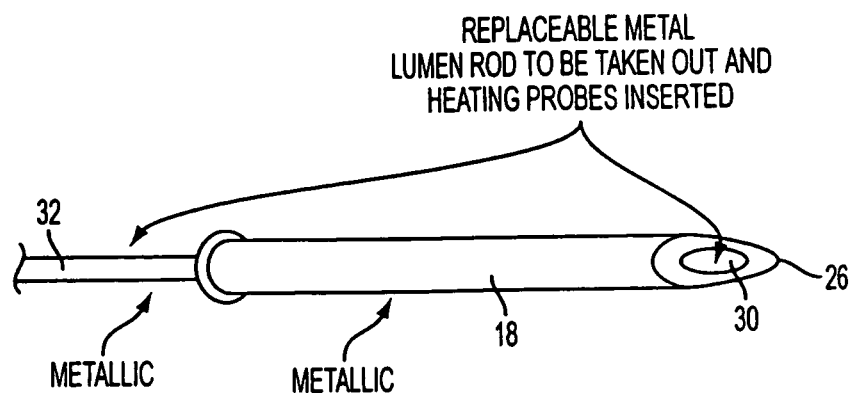
FIGS. 7A and 7B illustrate single metal introducer of heat/temperature sensor/delivery ports in another embodiment of an extended probe of the variable extended probe device of FIG. 1.
Figure 7B:
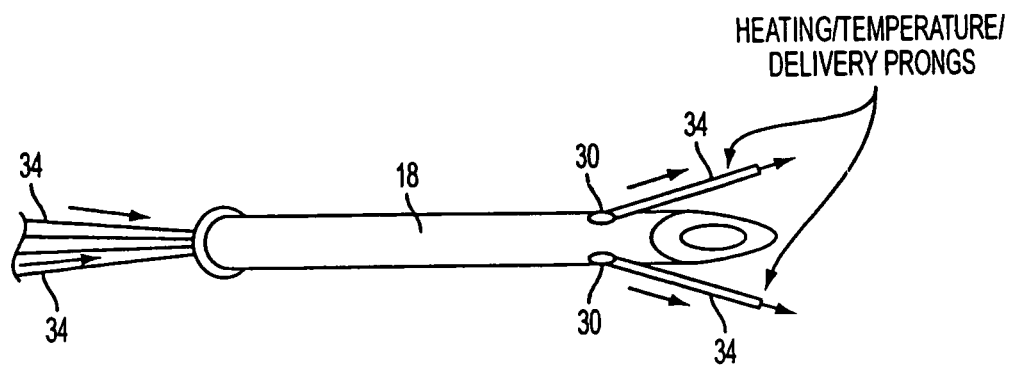

FIGS. 7A and 7B depict a further embodiment of an energy delivering probe 18 with a single metallic introducer energy delivery probe. In the embodiment depicted in 7A, a metallic rod 32 in inserted within the metallic energy delivery probe 18. The metallic rod 32 is removed once the probe 18 is adequately positioned in the treatment area of the patient's body and heating prongs 34 are inserted through the energy conduit 16 and through the energy delivery probe 18. FIG. 7B depicts the insertion of the heating prongs 34 into the energy delivery probe 18. In the embodiment of 7A, these prongs would exit the energy port 30 at the tip of the energy delivery probe 18. In the embodiment of 7B, these prongs exit the energy ports 32 along the side of the energy delivery probe 18.

Figure 8A:
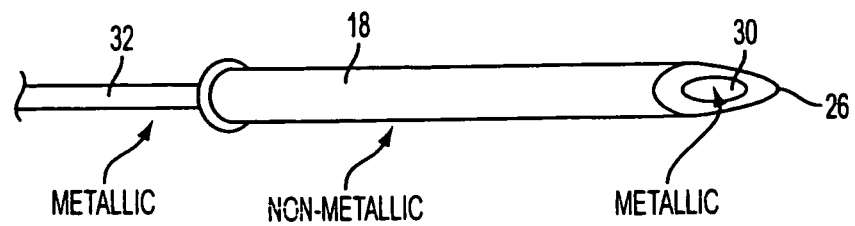
FIGS. 8A and 8B illustrate a single non-metallic introducer heat/temperature sensor/delivery ports in another embodiment of an extended probe of the variable extended probe device of FIG. 1.
Figure 8B:
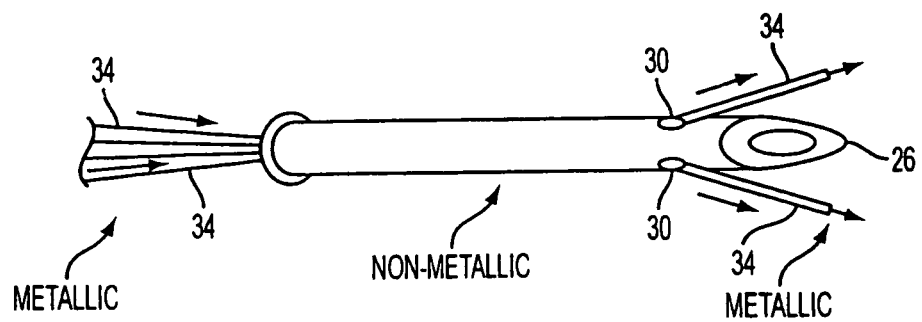

FIGS. 8A and 8B depict a further embodiment of an energy delivering probe 18 with a single non-metallic introducer energy delivery probe. In the embodiment depicted in 8A, a metallic rod 32 is inserted within the non-metallic energy delivery probe 18. The metallic rod 32 is removed once the probe 18 is adequately positioned in the treatment area of the patient's body and heating prongs 34 are inserted through the energy conduit 16 and through the energy delivery probe 18. FIG. 8B depicts the insertion of the heating prongs 34 into the energy delivery probe 18. In the embodiment of 8A, these prongs would exit the energy port 30 at the tip of the energy delivery probe 18. In the embodiment of 8B, these prongs exit the energy ports 30 along the side of the energy delivery probe 18. The heating prongs 34 of FIGS. 7B and 8B may also include temperature sensors.

Figure 9A:
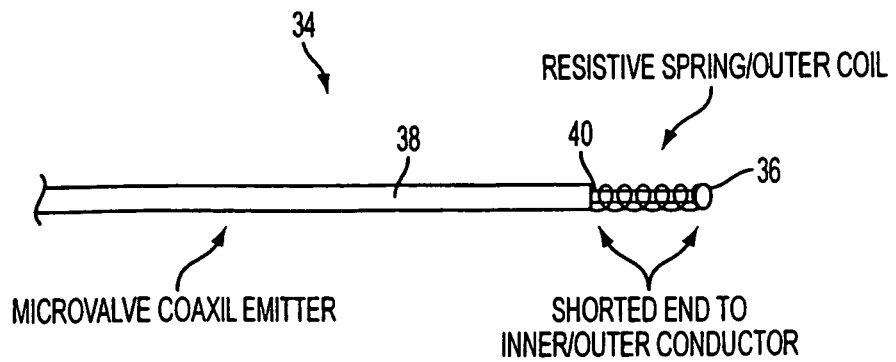
FIG. 9 is a unique microwave/resistive spring loaded short circuit antenna design that may be used in the probes of FIG. 1-8.
Figure 9B:
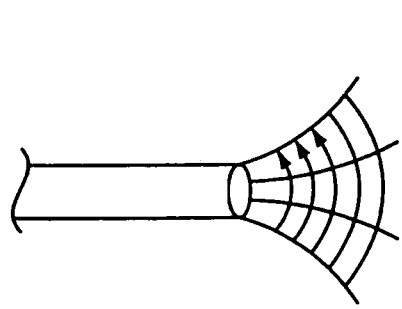
Figure 9C:
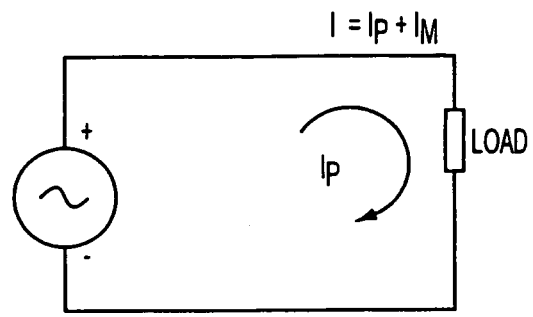
Figure 9D:
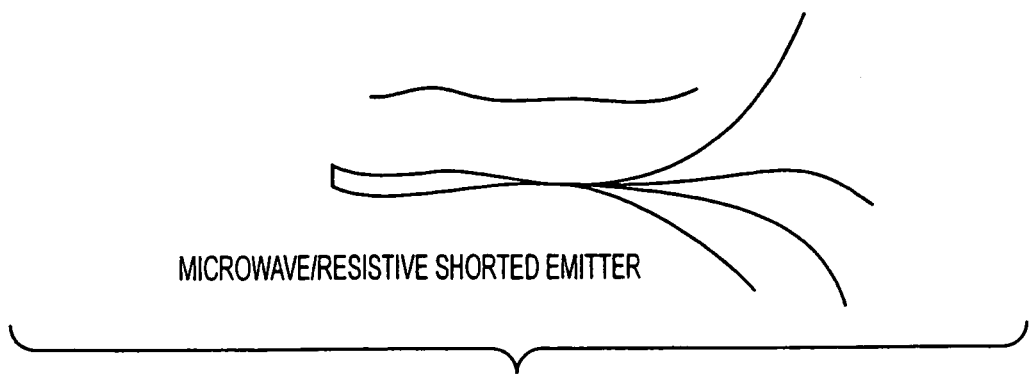

FIG. 9A depicts a unique microwave/resistive spring loaded short circuit antenna design that may be used as a heating prong 34. This improved heating prong, is provided with a resistive spring outer coil 40, and inner conductor 36, and an outer conductor 38. This unique arrangement when provided as the load in the circuit as shown in FIG. 9C provides a microwave-resistive shorted emitter as shown in FIG. 9D. This is an improved microwave emission over the prior art microwave emitter wave as shown in FIG. 9B. It not only heats with microwaves but the resistive spring load short delivers a direct current (DC). This new design overcomes the limitations of DC and MA technologies.

Figure 10A:
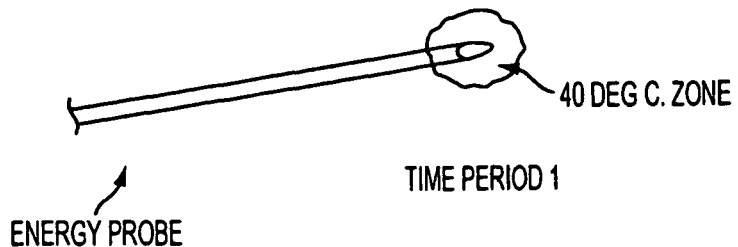
FIG. 10 illustrates the dynamic control of heat with a rigid temperature formulation release/activated drugs and/or gene and/or viral vectors.
Figure 10B:
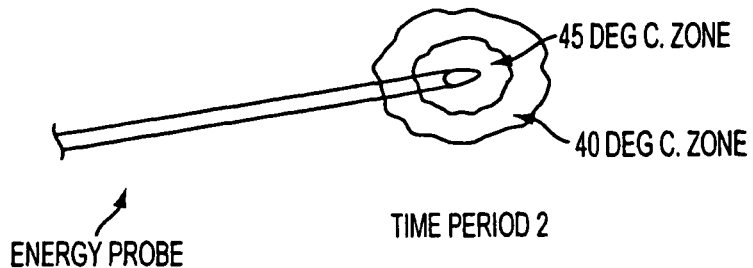
Figure 10C:
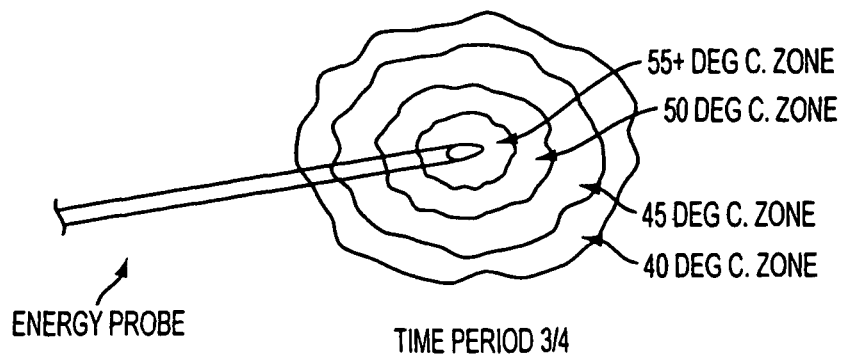

As illustrated in the four time periods shown in FIG. 10, an energy probe 10' is inserted in a bodily conduit and serves to heat tissue adjacent to the bodily conduit. Initially, when the energy probe 10' begins warming up the surrounding tissue, an approximately 40 degree C. zone radiates from the energy probe during time period 1. During a second time period, two heating ringed areas exist. One is the 40 degree C. zone, which has moved further from the energy probe 10' and the other is a 45 degree C. zone that is within the 40 degree zone surrounding the energy probe 10'. Over time periods 1-4, dynamic temperature profiles move out away from the energy probe 10' so that the highest temperature is the ringed area adjacent energy probe and the temperature decreases in temperature as the ringed areas move away from the energy probe 10'. As shown in FIG. 10, during time periods 3/4, the energy probe 10' heat the surrounding tissue in at least four different ringed temperature areas. The ringed area closest to the energy probe 10' may be an approximately 55 degrees C. zone and the temperature zones of the ringed areas decrease as they move away from the energy probe 10' so that an approximately 50 degree C. zone surrounds the innermost ringed area and an approximately 45 degree C. zone surrounds the approximately 50 degree zone. As the time periods illustrate, the initial temperature of approximately 40 degrees C. continues to move away from the energy probe 10' while new temperature zoned areas are created inside the outer 40 degree zone.

It is with this dynamic temperature profile that rigid temperature release formulations of the drugs and/or genes and/or viral vectors are released, activated and/or fixed in the relative 40 degree C. zone for each time period. That is, the thermoactivated drugs and/or genes and/or viral vectors are designed so that the drugs and/or genes and/or viral vectors are released, activated and/or fixed in the relative 40 degree C. zone. In that the 40 degree C. zone moves away from the energy probe 10', if the drugs and/or genes and/or viral vectors were injected prior to or during the heating, the drugs and/or genes and/or viral vectors would be activated at each 40 degree zone shown in each time period. This dynamic temperature profile determines when the drugs and/or genes and/or viral vectors are released or activated or fixed.

Figure 11:
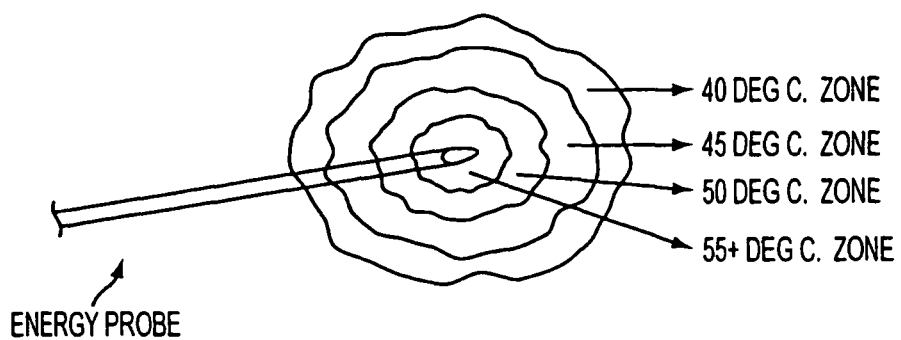
FIG. 11 illustrates the static and/or steady state heating profile with rigid temperature formulation release/activated drugs and/or genes and/or viral vectors.

FIG. 11 illustrates a static and/or steady state heating profile with rigid temperature formulation release/activated drugs and/or genes and/or viral vectors. Basically, FIG. 11 shows an energy probe 10' and how the tissue surrounding the probe is heated in a ringed area after the probe has be heated for a sufficient time period to reach a static or steady state temperature. This is similar to time period 3/4 of FIG. 10 where the highest temperature ringed area zone is the closest to the energy probe 10' and the temperature of the ringed areas decreases as they move away from the probe. The static or steady state heating profile is used to release the rigid temperature release formulations of drugs and/or genes and/or viral vectors in the outer temperature zone (approximately 40 degree C.) in order to effectively treat the margins of a tumor where the effects of thermotherapy may be limited. That is, the combined release, activation and/or fixation of drugs and/or genes and/or viral vectors and heat will improve the effectiveness of heat in killing the margins of a tumor.

Figure 12:
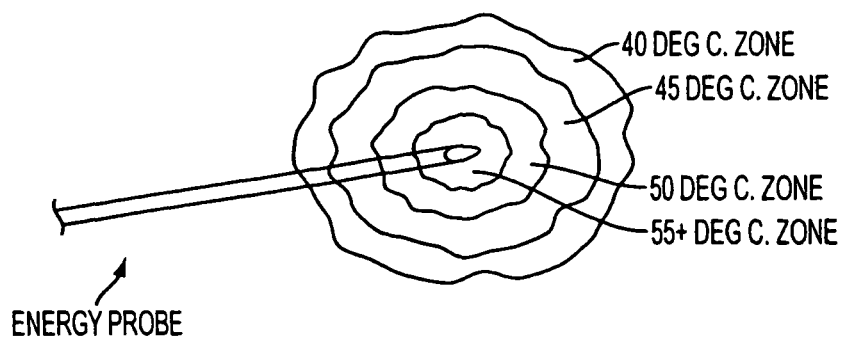
FIG. 12 illustrates the dynamic and/or static and/or steady state heating profile with broad temperature formulation release/activation drugs and/or genes and/or viral vectors.

FIG. 12 illustrates a dynamic and/or static and/or steady state heating profile with broad temperature formulation release/activation drugs and/or genes and/or viral vectors. During a dynamic and/or static and/or steady state heating profile, the release, activation and/or fixation of drugs and/or genes and/or viral vectors is designed to do so over a larger and broader temperature zone based on a broad temperature formulation range within a 0-15 degree C. tolerance. That is, the broad temperature formulation range within which the drugs and/or genes and/or viral vectors are released, activated and/or fixated may be approximately 40 degree C. to 55 degree C., or a smaller range of 40 degree C. to 45 degree C., or even a smaller range of 1-3 degrees C.

This new invention may also be effective for the treatment of cancer but also the non cancerous afflictions. This may hold true for the treatment of other sites, local and regional besides the above mentioned prostate gland. Thus may be advantages to be able to treat not only cancerous but non cancerous, precancerous as well as infectious diseases. Again, it will be to treat a localized or regional tumor such to activate/release both drugs and/or genes.

Although the present invention has been described with reference to preferred embodiments, workers skilled in the art will recognize that changes may be made in form and detail without departing from the spirit and scope of the invention.

I claim:

1. An apparatus for administering a focused treatment into a targeted tissue region of a patient's body comprising:
   a catheter comprising a distal tip adapted to penetrate the targeted tissue region within the body and at least one catheter port located at the distal tip;
   a plurality of adjustable probes moveably disposed within the catheter, each of the plurality of adjustable probes comprising a distal tip adapted to penetrate tissue, at least one of said adjustable probes being an energy delivering probe comprising one or more energy delivery ports;
   a plurality of heating prongs configured to extend out of the energy delivery ports of said at least one adjustable probe for treating differently shaped treatment zones; and
   a controller adapted for independently extending each of said plurality of adjustable probes out of the catheter port and into the targeted tissue region after the distal tip is inserted into the targeted tissue.

2. The apparatus according to claim 1 further comprising: one or more temperature sensors positioned at the tip of at least one or more of said plurality of adjustable probes.

3. The apparatus according to claim 1 further comprising: one or more fluid delivery ports positioned at the tip of at least one or more of said plurality of adjustable probes.

4. The apparatus according to claim 3, wherein said energy delivering probe is either metallic or non-metallic and includes an internal metallic rod that is removable from said energy delivering probe; and wherein said apparatus further includes one or more heating prongs which are capable of being inserted into said energy delivering probe once said metallic rod is removed from said energy delivering probe, said one or more heating prongs also capable of being extended out of the one or more energy delivery ports.

5. The apparatus according to claim 1 further comprising:
   an energy emitter for emitting energy through said one or more energy delivery ports;
   wherein said energy emitter heating prong emits energy using one or more of the methods selected from the group consisting of Radio Frequency Ablation (RFA), Microwave Ablation (MA), Laser Ablation (LA), Ultrasound Ablation (UA), Hi Energy Focused Ultrasound (HIFU), focused microwaves (FM), and combinations thereof.

6. The apparatus according to claim 1 further comprising:
   at least one or more temperature sensors positioned at the tip or along the length of at least one or more of said plurality of adjustable probes; and
   at least one or more fluid delivery ports positioned at the tip or along the length of at least one or more of said plurality of adjustable probes.

7. The apparatus according to claim 1, wherein said apparatus includes a plurality of said energy delivering probes.

8. The apparatus according to claim 1, wherein said plurality of adjustable probes are encased at least partially within said catheter, wherein each of said plurality of adjustable probes further includes at least one or more of the elements selected from the group consisting of a temperature sensor and a port for delivering a drug, gene, or viral vector, or an energy delivery port.

9. The apparatus according to claim 1, wherein said plurality of adjustable probes are encased at least partially within said catheter, wherein each of said plurality of adjustable probes includes a plurality of the elements selected from the group consisting of a temperature sensor, a port for delivering a drug, gene, or viral vector, or an energy delivery port, wherein said plurality of elements are positioned at the tip of said probes or along the length of said probes.

10. The apparatus according to claim 1, wherein plurality of adjustable probes extend out of said catheter port in one of a J-shaped array, oval-shaped array or linear array to fix and control the size and shape of a treatment zone so that the treatment is focused on the targeted tissue region and avoids damaging surrounding tissue.

11. The apparatus according to claim 1 further comprising:
   one or more temperature sensors disposed along the length of at least one or more of said plurality of adjustable probes.

12. The apparatus according to claim 1 further comprising:
   one or more fluid delivery ports disposed along the length of at least one or more of said plurality of adjustable probes.

13. The apparatus according to claim 1 wherein said at least one energy delivering probe comprises one or more energy delivery ports are disposed along the length of said at least one adjustable probe.

14. An apparatus for administering a focused treatment into a targeted tissue region of a patient's body comprising:
   an elongated body member having a distal end adapted to penetrate tissue;

a plurality of probes moveably disposed within the elongated body member, each of said plurality of probes comprising a distal tip adapted to penetrate tissue and being adjustable between a retracted position and an extended position, at least one of said probes being an energy delivering probe comprising one or more energy delivery ports;

a plurality of heating prongs configured to extend out of the one or more energy delivery ports of said energy delivering probe for treating differently positioned treatment zones; and a controller adapted for independently extending each of the plurality of probes beyond the distal end of the elongated body member into the targeted tissue region within the patient's body after the elongated body member is inserted into the targeted tissue region.

15. The according to claim 14 wherein the plurality of probes are at least partially housed within the elongated body member when the plurality of probes are in the retracted position.

16. The apparatus according to claim 15 wherein at least a portion of the plurality of probes extend beyond the distal end of the elongated body member when the plurality of probes are in the extended position.

17. The apparatus according to claim 14 wherein the elongated body member is hollow.

18. The apparatus according to claim 17 wherein the plurality of probes are completely housed within the elongated body member when the plurality of probes are in the retracted position.

19. The apparatus according to claim 17 wherein at least a portion of the plurality of probes extend beyond the distal end of the elongated body member when the plurality of probes are in the extended position.

20. The apparatus according to claim 14 wherein the plurality of probes extend out of the elongated body member in a J-shaped array.

21. The apparatus according to claim 14 wherein the plurality of probes extend out of the elongated body member in an oval-shaped array.

22. The apparatus according to claim 14 wherein the plurality of probes extend out of the elongated body member in a linear array.

23. The apparatus according to claim 14, further comprising:
a temperature sensor disposed on at least one of the plurality of probes.

24. The apparatus according to claim 14, further comprising:
a fluid delivery port disposed on at least one of the plurality of probes.

25. The apparatus according to claim 14 wherein the one or more heating prongs energy emitter emit energy using Radio Frequency Ablation.

26. The apparatus according to claim 14 wherein the one or more heating prongs energy emitter emit energy using Microwave Ablation.

27. The apparatus according to claim 14 wherein the one or more heating prongs energy emitter emit energy using Laser Ablation.

28. The apparatus according to claim 14 wherein the one or more heating prongs energy emitter emit energy using Ultrasound Ablation.

29. The apparatus according to claim 14 wherein the one or more heating prongs energy emitter emit energy using Hi Energy Focused Ultrasound.

30. The apparatus according to claim 14 wherein the one or more heating prongs energy emitter emit energy using focused microwaves.

* * * * *